United States Patent [19]

Sinha

[11] Patent Number: 5,767,407

[45] Date of Patent: Jun. 16, 1998

[54] NONINVASIVE IDENTIFICATION OF FLUIDS BY SWEPT-FREQUENCY ACOUSTIC INTERFEROMETRY

[75] Inventor: Dipen N. Sinha, Los Alamos, N. Mex.

[73] Assignee: The Regents of the University of California, Los Alamos, N. Mex.

[21] Appl. No.: 589,935

[22] Filed: Jan. 23, 1996

[51] Int. Cl.[6] .................... G01N 29/02; G01N 29/22
[52] U.S. Cl. .................... 73/579; 73/597; 73/599; 73/61.49; 73/61.79; 364/509
[58] Field of Search .................... 73/579, 589, 647, 73/597, 648, 599, 592, 659, 646, 19.03, 19.1, 631, 24.01, 32 A, 54.41, 602, 61.49, 61.75, 61.79, 64.53, 865.5, 645, 61.45, 64.42, 64.3, 630, 629; 209/155; 364/484, 506, 509

[56] References Cited

U.S. PATENT DOCUMENTS

| | | | |
|---|---|---|---|
| 4,706,509 | 11/1987 | Riebel | 73/865.5 |
| 5,255,564 | 10/1993 | Glad et al. | 73/597 |
| 5,359,541 | 10/1994 | Pope et al. | 364/497 |
| 5,369,979 | 12/1994 | Aylsworth et al. | 73/24.01 |
| 5,392,635 | 2/1995 | Cadet et al. | 73/24.01 |
| 5,473,934 | 12/1995 | Cobb | 73/61.49 |

OTHER PUBLICATIONS

Dipen N. Sinha et al., "Swept Frequency Acoustic Interferometry Technique for Chemical Weapons Verification and Monitoring," LA–UR–95–610, abstract presented at the Third International Conference On-Site Analysis held in Houston Texas on Jan. 22-25, 1995.

*Primary Examiner*—Hezron E. Williams
*Assistant Examiner*—Rose M. Miller
*Attorney, Agent, or Firm*—Samuel M. Freund

[57] ABSTRACT

A method for rapid, noninvasive identification and monitoring of chemicals in sealed containers or containers where direct access to the chemical is not possible is described. Multiple ultrasonic acoustic properties (up to four) of a fluid are simultaneously determined. The present invention can be used for chemical identification and for determining changes in known chemicals from a variety of sources. It is not possible to identify all known chemicals based on the measured parameters, but known classes of chemicals in suspected containers, such as in chemical munitions, can be characterized. In addition, a large number of industrial chemicals can be identified.

4 Claims, 5 Drawing Sheets

NONINVASIVE IDENTIFICATION OF FLUIDS BY SWEPT-FREQUENCY ACOUSTIC INTERFEROMETRY

FIELD OF THE INVENTION

The present invention relates generally to identification and monitoring of substances and, more particularly, to the noninvasive identification and monitoring of materials using the values of up to four parameters determined by swept-frequency acoustic interferometry. This invention was made with government support under Contract No. W-7405-ENG-36 awarded to The Regents of The University of California by the U.S. Department of Energy. The government has certain rights in the invention.

BACKGROUND OF THE INVENTION

Existing methods for identifying chemicals (fluids) involve various kinds of spectroscopy, chromatography, and standard chemical analyses. Such methods are not applicable when the chemicals are located inside of sealed containers and analysis must be performed noninvasively. One example would be the need for identifying chemical warfare agents inside munitions for both international treaty verification and compliance monitoring, and also for various nonproliferation purposes including counter-terrorism. In such situations, it is imperative that the operator not be exposed to chemical hazards and that the integrity of the container (e.g., artillery shells, bulk containers, etc.) is not affected.

Other situations include the monitoring of industrial chemicals flowing through pipes or kept in reaction vessels. In such situations, it is always desirable to use probes that do not penetrate the container. Firefighters need a simple way for determining whether a container found near a fire contains flammable or hazardous materials. Currently, there is no simple way to accomplish this task. Another possible application might be the identification of spoiled wine in bottles without opening them.

Although any physical characteristics of a fluid which can be noninvasively measured can be used for this purpose, ultrasonic interferometry techniques are well-suited for this purpose.

Ultrasonic interferometry techniques have been used for decades to measure sound speed and attenuation in liquids. Customized resonator cells have been designed for this purpose and generally include piezoelectric transducer disks which are disposed to form the opposite parallel walls of a resonator cavity. The liquid to be investigated is placed in direct contact with the transducers. For studying liquids inside sealed containers, it is not possible to form such a cavity and one is required to make measurements from outside the containers.

Noninvasive interferometry for containers in which the liquids to be investigated are ordinarily found pose problems that are not present in situations where the transducers are in direct contact with the liquid. Interferometry requires generating standing waves inside a cavity filled with the liquid. The widths of the interference peaks are a measure of sound energy loss in the cavity. If the walls are perfectly reflecting, then the observed loss is principally due to losses in the liquid, such as due to absorption of sound in the liquid. Such absorption varies as the square of the frequency up to approximately 100 MHz for most liquids. If the liquid is a suspension or an emulsion, additional losses due to sound scattering may be expected. This scattering loss is strongly frequency-dependent and also depends on the particle size distribution in the suspension. Observed attenuation of peaks at certain frequencies may be related to particle size, and this information can be used to determine the suspension characteristics. Such attenuation generally occurs below 10 MHz for most food products, such as milk and edible oils.

Frequency-dependent information is difficult to obtain using conventional pulse-echo techniques. First, such procedures require high speed and expensive digital oscilloscopes or digitizers to record the pulse waveform. Data recording must be followed by Fast Fourier Transform (FFT) methods to convert the data into the frequency domain. However, since all frequencies contained in the sharp pulse applied to the liquid sample are not faithfully transferred into the liquid because of the interface mismatch at the transducer-container boundary, essential frequency information is lost, and the resulting data provide unreliable results. Moreover, ringing of the pulse inside the container wall itself makes time-of-flight measurements difficult and in many cases inaccurate. If the liquid path length is small, as is the case in 105 mm artillery shells, it is extremely difficult to resolve the pulse return signal through the liquid path from this wall ringing. Interferometry suffers from none of these problems and the signal-to-noise ratio of the resulting data is several orders of magnitude higher than that which is obtained from pulse-echo measurements.

Specific gravity of solutions located in selected structures has been measured by obtaining the resonance response spectrum of the fluid/structure over a range of frequencies that is outside of the response of the structure itself, as described in U.S. Pat. No. 5,359,541 for "Fluid Density And Concentration Measurement Using Noninvasive In Situ Ultrasonic Resonance Interferometry," which issued to Noah G. Pope et al. on Oct. 25, 1994. A Fast Fourier Transform of the resonance response spectrum is then performed to form a set of Fast Fourier Transform values. A peak value for the transform is determined which may be related to the specific gravity of the fluid solution. For measurements over the selected frequency range, the Pope et al. invention teaches that the number of resonance peaks will decrease with increasing concentration, since the velocity increases with concentration and, hence, the interval between resonance peaks increases.

Accordingly, it is an object of the present invention to provide a noninvasive method for determining certain fluid parameters using ultrasonic interferometry which does not require contact between the ultrasonic transducers and the fluid under investigation, and one in which accuracy is not compromised by difficult-to-perform pulse echo measurements.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the method for noninvasively identifying and/or monitoring fluids in a closed container of this invention may include the steps of: introducing periodic ultrasonic energy having a chosen frequency through the walls of the container from the outside thereof, thereby establishing a standing-wave vibrational pattern in the fluid; sweeping the chosen frequency through a selected range of frequencies; measuring the spacing between the features of the standing-wave vibrational pattern which relate to the fluid; and measuring the full-width-at-half-maximum of the features of the standing-wave vibrational pattern which relate to the fluid, whereby the speed of sound and the attenuation of sound waves in the fluid can be determined.

It is preferred that the full-width-at-half-maximum of the features of the standing-wave pattern as a function of the square of the applied frequency also be measured.

BRIEF DESCRIPTION OF THE DRAWINGS

The accompanying drawings, which are incorporated in and form a part of the specification, illustrate the embodiments of the present invention and, together with the description, serve to explain the principles thereof. In the drawings.

DETAILED DESCRIPTION

Figure 1:
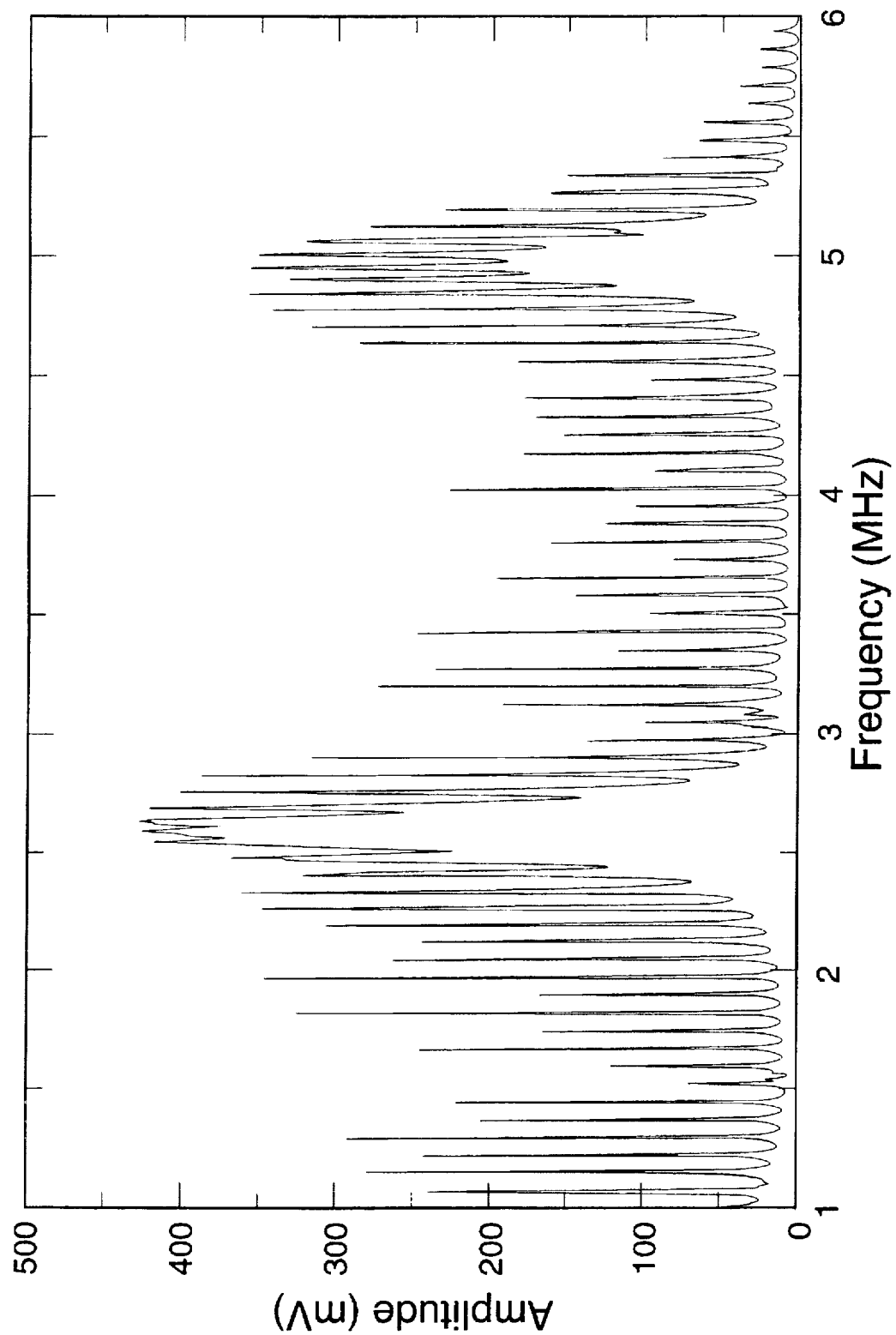
FIG. 1 is a typical interference pattern derived from a glass container holding a fluid (water) between two walls, showing the standing waves inside the liquid cavity (sharp) as well as those in the wall of the container (broad).

Briefly, the present invention includes the use of external transducers to introduce a standing-wave ultrasonic vibrational pattern into a fluid enclosed in a container over a range of frequencies, and to determine certain characteristics of this pattern from which (a) speed of sound; (b) the sound attenuation; (c) liquid density; and (d) the frequency dependence of sound absorption in the liquid, may be determined. These four parameters (or a subset of these) can be used to identify a large number of chemical compounds. Variations from the measured physical properties of any given liquid (e.g., due to deliberate dilution, mixing with other substances, contamination due to material leaking into the container, aging of chemicals, breakdown of chemicals, etc.,) can also readily be detected. Noninvasive measurements can be made in cylindrical containers or containers with liquid in annular spaces, such as in artillery shells for chemical munitions. Container wall thickness can vary from the thinnest wall consistent with the structural integrity of the container, to relatively large (~2 cm). Walls thicker than approximately 2 cm for cylindrical containers generate spurious interference due to shear waves propagating through the walls themselves along the circumference. In many situations, this can be subtracted out but not for all types of containers. Containers can be made from any stiff material, such as metals, plastics (polypropylene, polyethylene, etc., commonly used as industrial chemical containers). Also, the size of the container can vary from small (e.g., 1 mL volume optical cells) to large containers (e.g., 55-gallon drums, 1-Ton bulk containers for chemical warfare compound storage). Larger containers than these generate overlapping interference peaks which makes determining peak widths accurately difficult, although sound speed can still be measured accurately.

Most common chemical warfare agents can be uniquely identified if multiple physical properties are determined. Each fluid (liquid, mixture, emulsion, gas, suspensions) has characteristic frequency-dependent ultrasonic properties. It is possible for any two fluids to have one or more similar properties. However, if multiple properties are simultaneously employed, the fluid identification becomes much more certain in terms of those properties, especially if these are independent physical parameters. Other properties that can be used include acoustic nonlinearity and molecular relaxation times. Unfortunately, acoustic nonlinearity and molecular relaxation times are difficult to extract from noninvasive measurements and require well-controlled measurement techniques. Depending on the application, it is possible to easily measure up to four parameters using the method of the present invention.

The interference spectrum may also be used as a characteristic acoustic (ultrasonic) signature for detecting small changes with time (e.g., aging) and for verifying an exact match of an item with its own previous signature to determine whether tampering has occurred. The matching may be accomplished by time-series (interference spectrum) cross-correlation. Internal variations, such as rusting or other deposition on the inside wall of the container can also be detected by observing any is changes in the wall interference peak for a particular container as a function of time.

Noninvasive interferometry in containers introduces problems that are not present in the situation where the transducers are in direct contact with the liquid to be tested. When standing waves are generated inside of a cavity filled with liquid, the interference peak widths represent the sound energy loss in the cavity. If the walls were perfectly reflecting, then this loss would represent losses in the liquid, such as due to absorption of sound in the liquid. Absorption varies as frequency-squared to approximately 100 MHz for most liquids.

If a fluid-filled cavity, formed by the walls of two opposing piezoelectric transducers, is excited by sound, standing waves can be set up inside the fluid if the wavelength of the sound wave is an integral number of half-wavelengths. One transducer is used as the transmitter to which an electrical signal is applied to generate sound pressure waves inside the cavity, whereas the second transducer is used as a receiver to detect the standing waves, the so-called cavity resonances. A series of equidistant (in frequency) resonance (interference) peaks can be observed if the excitation signal is a periodic oscillatory wave form that is swept in frequency to cover a wide frequency range. The spacing between any two adjacent peaks is directly proportional to the sound speed in the liquid at the median frequency of the two peaks. The full-width-at-half-maximum of any resonance peak is related to the sound attenuation in the liquid at the peak frequency. Thus, by using a swept-sine wave excitation, both sound speed and sound attenuation for a fluid (liquid, mixture, emulsion, suspension, etc.) can be determined simultaneously over a wide frequency range. Both transducers may be located on one side of the container if access is a problem.

When the transducers cannot be placed in contact with the fluid, the transducer system is placed on the outside of the container wall, and measurements must be made from the outside of the container. The fluid under investigation is contained in the space between the two walls, and the observed interference (standing wave) pattern now has two superimposed components; in addition to the standing waves generated inside the liquid cavity, one observes standing wave patterns in the wall thickness of the container.

Figure 2:
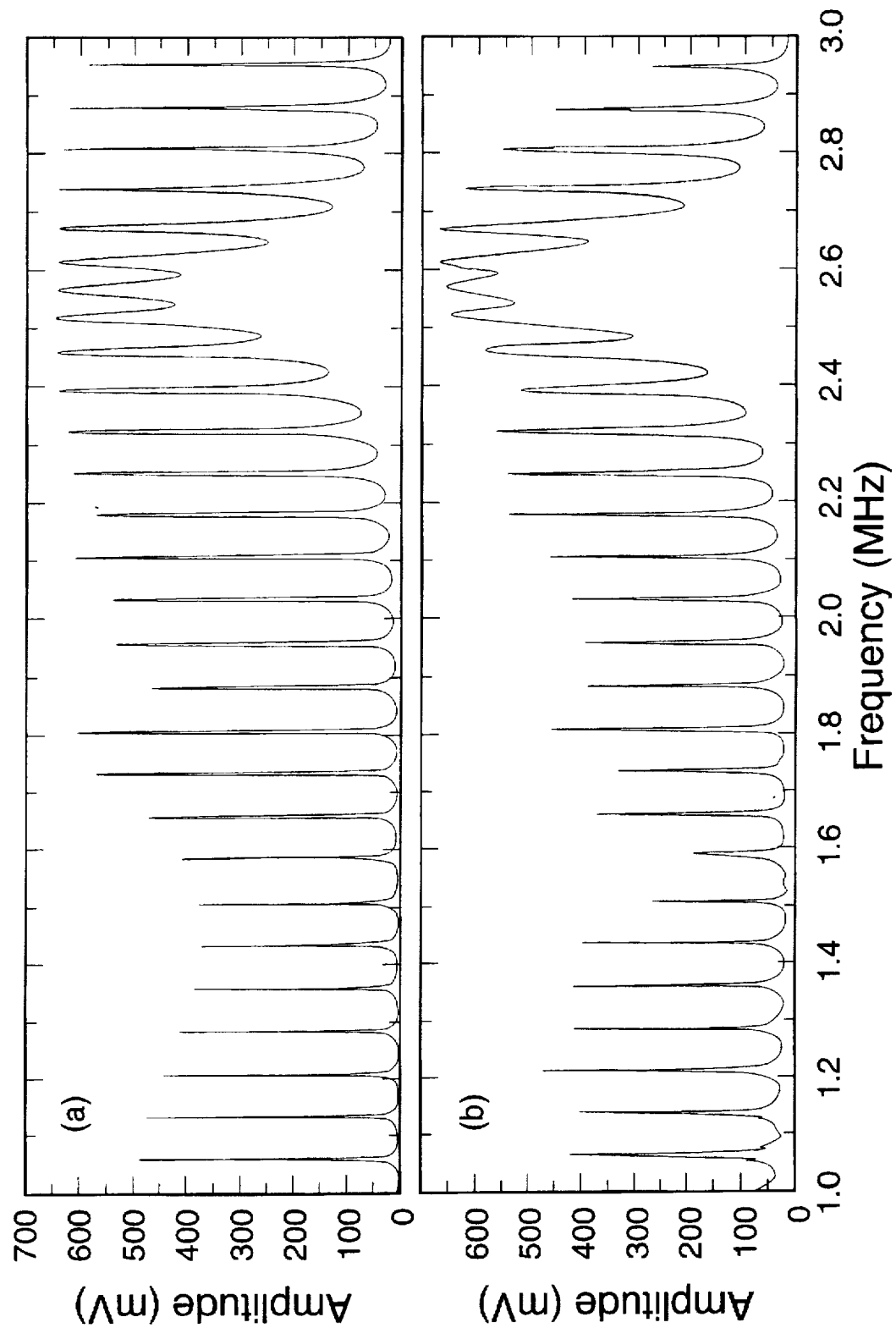
FIG. 2 is a comparison of an interference pattern taken at higher resolution in the cell used in FIG. 1, hereof (FIG. 2a) containing water, with a predicted pattern using a one-dimensional wave propagation through multiple boundaries (FIG. 2b).

Reference will now be made in detail to the present preferred embodiments of the invention, examples of which are illustrated in the accompanying drawings. An example of the superposition of wall and fluid standing wave patterns is shown in FIG. 1, hereof, where the data were taken in a water-filled glass cell (1.25 mm thick, approximately parallel walls, 1 cm apart), and where the transducers were placed on opposing walls of the cell. An identical spectrum is observed if a dual-element transducer is located on one side of the cell. The interference peaks in the glass wall (broad features) are clearly distinguishable from those of the liquid. This is because the speed of sound and the path length are different for the liquid and the glass wall: FIG. 2a shows a portion of the observed spectrum shown in FIG. 1 hereof, compared with predictions from a theoretical model (FIG. 2b) for the water-filled, glass resonator system. This theoretical model is based on one-dimensional wave propagation through multiple boundaries and was developed by the present inventor specifically to understand the underlying physics of the present invention. As can be seen from FIG. 2, the agreement with the experimental data is excellent. By using this theoretical model one can readily extract the sound speed and sound attenuation values of the liquid inside the resonator cell. A more complex model is required to derive similar information from cylindrical cells, such as chemical munitions with burster cores, pipes, and simple cylindrical objects. Because frequency measurements can be made very accurately and with very high resolution (e.g., 0.1 Hz at 1 Mhz), the swept-frequency interferometry approach provides an excellent way to make these measurements. For all realistic containers, the liquid peaks are well separated from the wall peaks and pose no problem. In the rare situations where they overlap, theoretical analysis can extract the relevant parameters.

Having generally described the present invention, the following example illustrates the specific details thereof.

EXAMPLE

The instrumentation required for the interferometry measurements of the present invention is simple, and includes three primary components: (1) A transducer system; (2) A frequency-response analyzer having a chosen frequency range; and (3) A computer for data-analysis. The transducer system employed for the present measurements was made from two rectangular-shaped wide-band piezoelectric transducers mounted side by side inside a holder with the front face of the transducers covered with a thin layer of natural rubber. A small amount of grease or any ultrasonic coupling agent is used between the rubber layer and the transducer faces. The transducers are mounted at a slight angle to each other so as to enable them to be positioned radially on curved surfaces (e.g., artillery shells). The natural rubber provides excellent coupling between the transducers and the container. One of the transducers is used as the transmitter whereas the other is used as the receiver. A commercially available digital synthesizer and analyzer includes of all the necessary electronics for frequency sweep and signal processing. The frequencies employed were typically between 1 and 10 MHz. This frequency range is well beyond any structural resonance frequencies of the container, and one observes only the interference patterns set up in the wall thickness and the liquid inside the container. Thus, the apparatus directly probes the liquid. At these high frequencies the sound propagates in a beam with the dimensions of the transducers and proceeds along a straight line path through the liquid.

Figure 3:
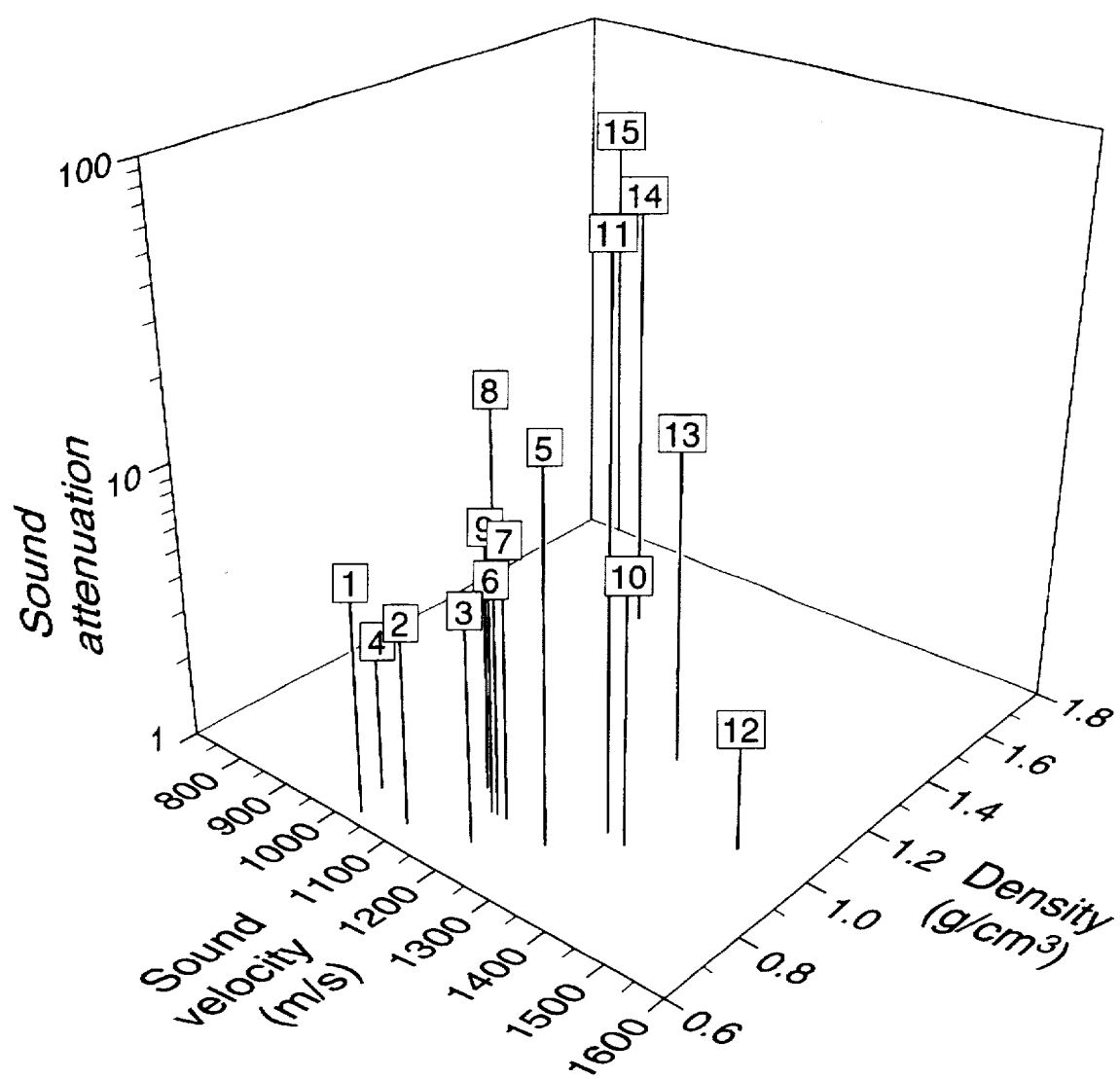
FIG. 3 shows the clear separation for identification purposes of several industrial liquids having similar acoustical properties using three measured parameters.

The computer records the data in real-time as the frequency sweep measurement is carried out in less than 1 minute. As soon as the sweep is finished, the parameter extraction takes place. Once the physical parameters are determined from the measurement, the values are compared with a database and the fluid, or changes therein is identified. Measurements on several common chemicals are shown in FIG. 3, hereof in a 3-D plot. The numbers represent the following compounds: 1. Pentane; 2. Hexane; 3. Octane; 4. Ethyl ether; 5. Cyclohexane; 6. Acetone; 7. Methanol; 8. Isopropanol; 9. Ethanol; 10. Toluene; 11. Benzene; 12. Water; 13. Chlorobenzene; 14. Chloroform; and 15. Perfluoro-methyl-cyclohexane. Sound speed was determined from the peak spacing of the interference pattern. The sound attenuation values are expressed in terms of the peak width, and the density is the extracted value from the frequency dependence of peak width (i.e., attenuation), as will be described in more detail hereinbelow. As can be seen, when plotted as a function of multiple physical parameters, the chemical compounds are well separated. Instead of density, one can substitute the frequency dependence of peak width, or add this parameter to the other three.

Of primary interest is the determination of sound speed and sound attenuation from the measured interference spectrum. As discussed earlier, it is straightforward to separate the interference peaks for the container wall from the liquid peaks. Because the frequency dependence of sound speed is negligible below 10 MHz for most liquids, the peak spacing (proportional to sound speed) does not change with frequency in the measured range. The peak full-width-at-half-maximum (related to sound attenuation), on the other hand, varies as frequency-squared. However, if we subdivide the measured frequency range into small subranges then over such a small sub-range one can safely assume the sound attenuation to be constant for all practical purposes. Thus, one can determine an average peak width for any given sub-range.

In most cases, autocorrelation is used as the data extraction process for the observed data at various frequency intervals. This process is fast and provides excellent results even for data that have significant associated noise. Essentially, the autocorrelation technique (i.e., correlating the spectrum with itself) provides an average spacing for the peaks and an average value of the peak full-width-at-half-maximum over a given frequency range. The autocorrelation shows a single peak and the position of this peak is the average peak spacing, $\Delta f_0$, of the spectrum shown earlier in FIG. 2a, hereof. If the path length, L, is known from the geometry of the container, the sound speed can be evaluated as:

$$C_{liquid} = 2 \times \text{path length} \times \text{peak spacing} = 2L\Delta f_0 \qquad (1)$$

The autocorrelation peak full-width-at-half-maximum is related to sound attenuation. The autocorrelation process is repeated over several frequency intervals and the averaged frequency dependent parameters are extracted. For the frequency value, the mid-frequency of the sub-range is used. Alternatively, the theoretical model can be fitted to the data using a nonlinear least-squares curve fitting technique where all parameters are determined from the fitted values.

However, this process is computationally intensive and the autocorrelation technique has been found to be faster and well-suited to practical applications.

Mathematically, the autocorrelation R(m) of a discrete time-series $f_n$ is defined as $$R(m) = \frac{1}{N-m} \sum_{n=0}^{N-m-1} f_n f_{n+m}, \quad m = 0, 1 \ldots M \quad (2)$$

This is simply the lagged product sum of the time series. In Eq. (2), the $f_n$ are the measured spectrum amplitudes at each frequency step corresponding to n, N is the total number of data points and M is called the time-lag (or lead). M is usually much less than N. The autocorrelation is thus another time-series of length M. The frequency lag value corresponding to the first peak amplitude in the autocorrelation is the average peak spacing and the width of the autocorrelation is directly related to the average full-width-at-half-maximum of the peaks.

Figure 4:
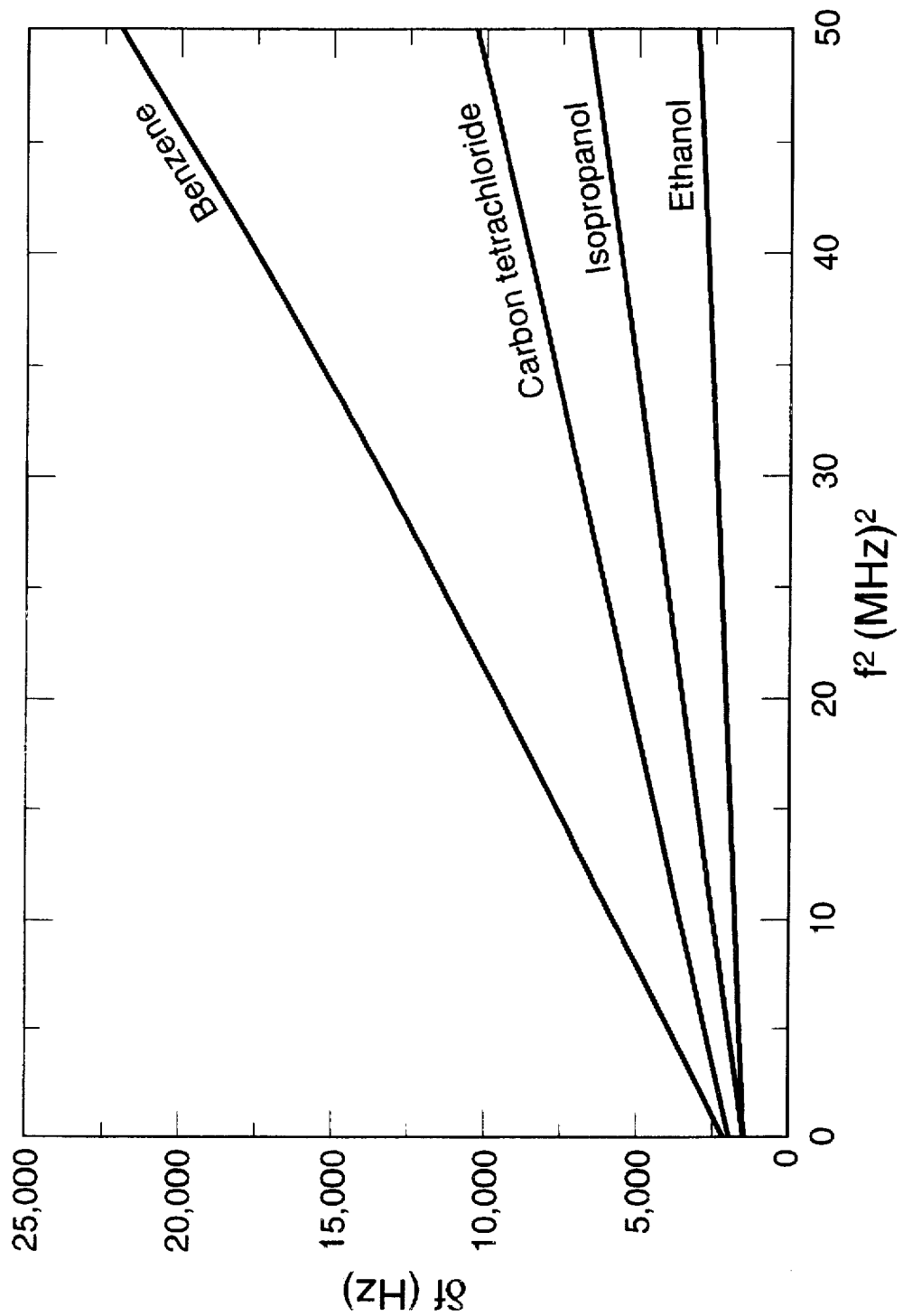
FIG. 4 is a plot of the linewidth as a function of the square of the frequency of the applied excitation for several liquids.

Similar information can be obtained from an FFT analysis of the data. However, an FFT unnecessarily carries out calculations that are not needed, and is more time consuming. On the other hand, a discrete autocorrelation is much faster computationally if the time-series (spectrum) is not too long. Sound attenuation in liquids varies as the square of the frequency. FIG. 4 shows experimental data for a several chemicals. This frequency dependence allows the determination of the liquid density. Because of the acoustic impedance, Z, (density×sound speed) mismatch between the liquid and the container wall, there is always leakage of energy through the wall. If the impedances between the liquid and the wall are very different, then the leakage is small; otherwise, it can be significant. This means that perfect standing waves are not set up due to the wall reflection loss. This wall loss contributes to the observed peak full-width-at-half-maximum in the interference spectrum. Thus, the observed peak full-width-at-full-maximum is a combination of two factors: (1) wall loss, and (2) absorption of sound in the liquid. Normally these two factors cannot be isolated unless is measurements are made over a wide frequency range. However, at zero (extrapolated) frequency, the peak full-width-at-half-maximum is only due to wall loss produced by the impedance mismatch. To extract the true sound absorption in the liquid, the intercept value is subtracted from all the peak width measurements. Since the sound speed of the liquid is independently determined by the peak spacing measurement, the liquid density can be determined if the wall material is known (i.e., the impedance of the wall material is known). Thus, both the slope and the intercept of the line in FIG. 4 can provide physical parameters. The slope is different for different liquids and can be used as a liquid specific physical parameter for identification.

As mentioned above, the extrapolated intercept value of peak width at zero frequency is due to impedance mismatch. There are four parameters involved: sound speed and density of the liquid, and those of the wall material. If the wall material is known (i.e., its sound speed and density are known), which is true in most cases and, particularly, for the chemical munitions (steel), then only the liquid density is unknown. The sound speed of the liquid is easily determined from the interference spectrum using the peak spacing. The peak spacing (sound speed) does not depend on the wall material, i.e., loss of energy through the wall material. Thus, the only unknown, the liquid density, can be extracted from the intercept from the peak full-width-at-half-maximum vs. frequency plot.

The underlying basis of the theory to explain the observed interference pattern is straightforward. Most books on Acoustics solve the problem of sound transmission through multiple layered media. The examples universally given in standard textbooks are for a finite thickness layer bounded by two identical media of infinite extent. In the present situation, we have a finite thickness liquid media bounded by two walls of the container. By including the additional boundary conditions of the two metal walls and solving for the sound transmission coefficient as a function frequency, a more complicated expression than the simple case given in text books may be derived. The boundary conditions are simply equating the pressure and the particle velocity at the boundary between any two media (e.g., metal—liquid, etc.,) on both sides. The analytical expression is very complex and, therefore, two approaches are possible: (1) A numerical solution of the entire problem is employed which takes several seconds of running time on a Pentium PC; or (2) A simplified analytical expression that is accurate to better than 1 percent when compared with the numerical solution is used to fit individual peaks.

Depending on the accuracy needed, one can use either approach. For extremely accurate work, the complete numerical solution that contains the wave equations and boundary conditions is employed. Even in this case, the autocorrelation approach is used to derive the initial guess values for each parameter for a non-linear least-squares curved fitting. Such initial guesses improve the convergence of the least-squares curve fitting by at least one order of magnitude and allows such fitting procedure to be carried out on a simple PC. However, the simple autocorrelation approach has been found to be extremely efficient and quite accurate for most practical purposes. For less stringent requirements, a simple look up table may be sufficient. Using the simplified analytical expression approach, it can be shown that:

$$\delta f_0 / \Delta f_0 = 4/\pi \times Z_{liquid}/Z_{wall}, \quad (3)$$

where $\delta f_0$ is the peak full-width-at-half-maximum when extrapolated to zero frequency, where there is no absorption of sound, $\Delta f_0$ is as defined in Eq. 1, $Z_{liquid} = C_{liquid} \, \rho_{liquid}$, and $Z_{wall} = C_{wall} \, \rho_{wall}$. Since $C_{liquid}$ is independently measured using the liquid peak spacing, and $C_{wall} \, \rho_{wall}$ can be determined from knowledge of the wall material or by calibration, $\rho_{liquid}$ can be determined.

Figure 5:
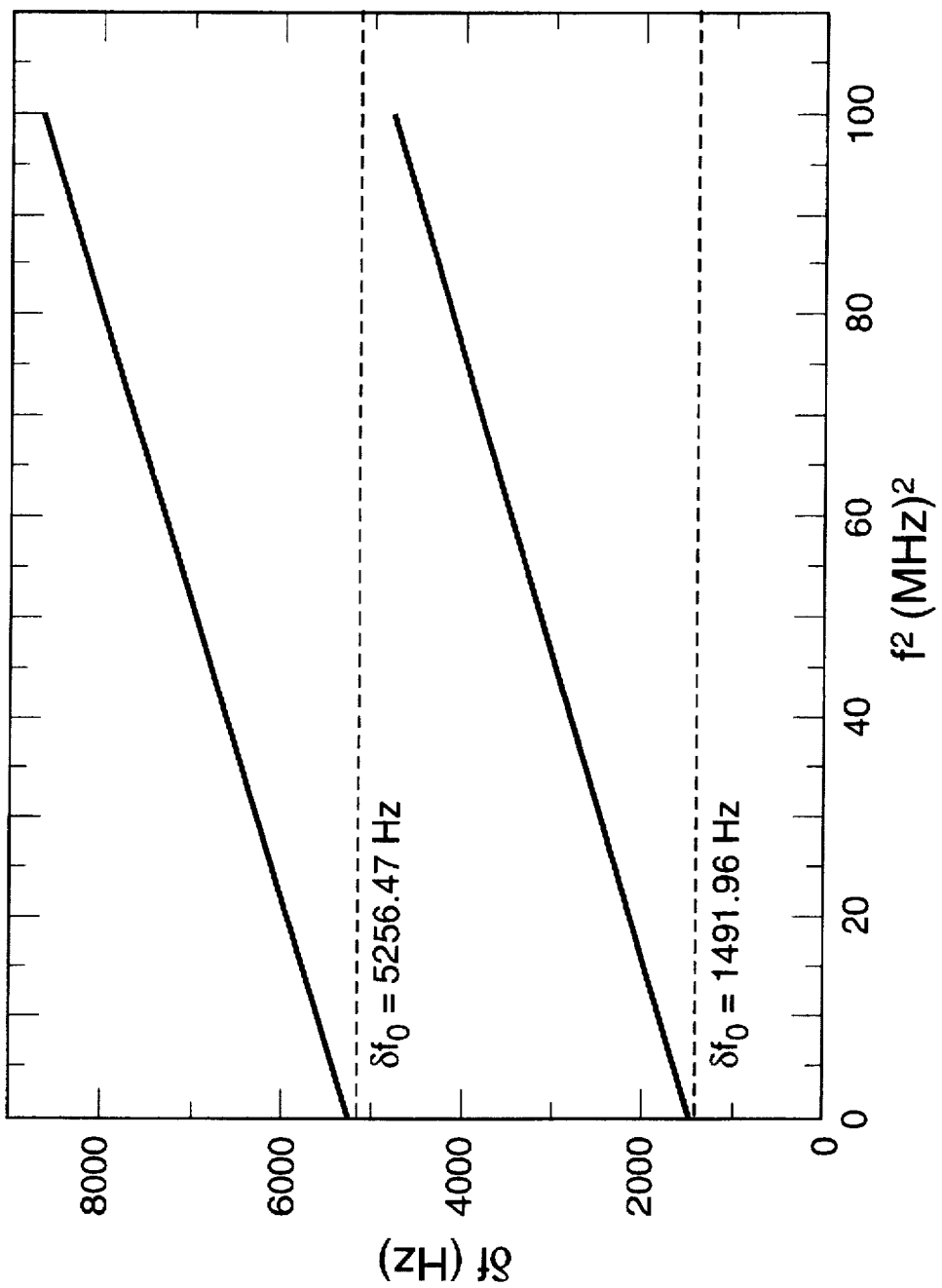
FIG. 5 is a plot of the linewidth as a function of the square of the frequency of the applied excitation for ethanol in a glass container (upper curve) and in a steel container (lower curve).

FIG. 5 shows a plot of the resonance line-full-width-at-half-maximum as a function of the square of the applied excitation for ethanol in a glass container (upper curve) and in a stainless steel container (lower curve). For the glass container $Z_{wall}/Z_{liquid}=14.04$, while for the stainless steel container, $Z_{wall}/Z_{liquid}=49.10$. The slopes of the curves are identical.

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the is principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for noninvasive identification of fluids in a closed container using swept-frequency ultrasonic interference, which comprises the steps of:

a. introducing periodic ultrasonic energy having a chosen frequency through the walls of the container from the outside thereof, thereby establishing a standing-wave vibrational pattern in the fluid;

b. sweeping the chosen frequency through a selected range of frequencies;

c. measuring the spacing between the features of the standing-wave vibrational pattern which relate to the fluid;

d. measuring the full-width-at-half-maximum of the features of the standing-wave vibrational pattern which relate to the fluid, whereby the speed of sound and the attenuation of sound waves in the fluid are determined; and e. identifying the fluid from the measured speed of sound and attenuation of sound waves in the fluid.

2. The method for noninvasive identification of fluids in a closed container using swept-frequency ultrasonic interference as described in claim 1, further comprising the step of measuring the full-width-at-half-maximum of the features of the standing-wave vibrational pattern which relate to the fluid as a function of the square of the applied frequency, whereby the density of the fluid is determined from an extrapolation of said measurements to zero applied frequency and knowledge of the impedance of the container walls, the density of the fluid and the slope of the resulting full-width-at-half-maximum versus frequency-squared curve being identifying parameters for the fluid.

3. A method for noninvasive monitoring of fluids in a closed container using swept-frequency ultrasonic interference, which comprises the steps of:

a. introducing periodic ultrasonic energy having a chosen frequency through the walls of the container from the outside thereof, thereby establishing a standing-wave vibrational pattern in the fluid;

b. sweeping the chosen frequency through a selected range of frequencies;

c. measuring the spacing between the features of the standing-wave vibrational pattern which relate to the fluid;

d. measuring the full-width-at-half-maximum of the features of the standing-wave vibrational pattern which relate to the fluid, whereby the speed of sound and the attenuation of sound waves in the fluid are determined;

e. comparing the speed of sound and the attenuation of sound waves in the fluid with standard values for these parameters; and f. monitoring the fluid by identifying changes in the speed of sound and in the attenuation of sound waves from the standard values for these parameters.

4. The method for noninvasive monitoring of fluids in a closed container using swept-frequency ultrasonic interference as described in claim 3, further comprising the steps of measuring the full-width-at-half-maximum of the features of the standing-wave vibrational pattern which relate to the fluid as a function of the square of the applied frequency, whereby the density of the fluid is determined from an extrapolation of said measurements to zero applied frequency and knowledge of the impedance of the container walls, the density of the fluid and the slope of the resulting full-width-at-half-maximum versus frequency-squared curve being monitoring parameters for the fluid, and comparing these monitoring parameters with standard values therefor, whereby changes in the fluid are identified.

* * * * *